(12) United States Patent
Cure et al.

(10) Patent No.: US 10,111,823 B2
(45) Date of Patent: Oct. 30, 2018

(54) SHAVE CREAM FORMULATION

(71) Applicant: GetCo LLC, Windsor, CO (US)

(72) Inventors: Michael R. Cure, Windsor, CO (US); Peter Curtis, Riverside, CA (US)

(73) Assignee: GETCO LLC, Windsor, CO (US)

(*) Notice: Subject to any disclaimer, the term of this patent is extended or adjusted under 35 U.S.C. 154(b) by 39 days.

(21) Appl. No.: 15/147,545

(22) Filed: May 5, 2016

(65) Prior Publication Data

US 2016/0324754 A1   Nov. 10, 2016

Related U.S. Application Data

(60) Provisional application No. 62/157,937, filed on May 6, 2015.

(51) Int. Cl.

| | | |
|---|---|---|
| A61K 8/73 | (2006.01) | |
| A61Q 9/02 | (2006.01) | |
| A61K 8/37 | (2006.01) | |
| A61K 8/34 | (2006.01) | |
| A61K 8/31 | (2006.01) | |
| A61K 8/36 | (2006.01) | |
| A61K 8/97 | (2017.01) | |
| A61K 8/41 | (2006.01) | |
| A61K 8/86 | (2006.01) | |
| C09K 15/18 | (2006.01) | |
| A61K 8/45 | (2006.01) | |
| A61K 8/67 | (2006.01) | |
| A61K 8/81 | (2006.01) | |

(52) U.S. Cl.
CPC ............... *A61K 8/731* (2013.01); *A61K 8/31* (2013.01); *A61K 8/34* (2013.01); *A61K 8/342* (2013.01); *A61K 8/345* (2013.01); *A61K 8/361* (2013.01); *A61K 8/37* (2013.01); *A61K 8/375* (2013.01); *A61K 8/41* (2013.01); *A61K 8/45* (2013.01); *A61K 8/678* (2013.01); *A61K 8/8147* (2013.01); *A61K 8/86* (2013.01); *A61K 8/97* (2013.01); *A61Q 9/02* (2013.01); *C09K 15/18* (2013.01)

(58) Field of Classification Search
None
See application file for complete search history.

(56) References Cited

U.S. PATENT DOCUMENTS 8,048,920 B2 * 11/2011 Joerger ................... A61Q 5/02
                                                         424/520
9,636,405 B2 * 5/2017 Tamarkin ............... A61K 47/10

* cited by examiner

*Primary Examiner* — Susan T Tran
(74) *Attorney, Agent, or Firm* — Steptoe & Johnson LLP (57) ABSTRACT

Shaving cream formulations can extend the life of shaving blades.

3 Claims, 5 Drawing Sheets

SHAVE CREAM FORMULATION

CLAIM OF PRIORITY

This application claims priority to U.S. Provisional Patent Application No. 62/157,937, filed May 6, 2015, which is incorporated by reference in its entirety.

TECHNICAL FIELD

This invention relates to shave cream formulations.

BACKGROUND

Shave cream has to meet a number of customer satisfaction criteria to be accepted by consumers. A shave cream needs to be safe and effective. A shaving cream formulation can affect the life of shaving blades.

SUMMARY

In one aspect, the invention relates to a shaving cream composition that extends blade life. In certain embodiments, the composition also improves comfort to the user.

A shaving cream composition can include water, carbomer, a palmitate ester, a glycerin, glyceryl acrylate/acrylic acid, a C8-C24 hydrocarbon, a fatty acid, butylene glycol, a c1-c4 alcohol, a fatty alcohol, a polyoxyethylene ether, a C3-C6 diol, Brassica Campestris, phenoxyethanol, tetrahydroxypropyl ethylenediamine, Aloe Barbadensis, carboxymethyl hydroxyehylcellulose, a monocyclic sesquiterpene alcohol, and tocopheryl acetate.

In one aspect, a shaving cream composition can include water, carbomer, ethylhexyl palmitate, glycerin, glyceryl acrylate/acrylic acid, isododecane, stearic acid, butylene glycol, ethyl alcohol, cetearyl alcohol, ceteareth-20, propanediol, Brassica Campestris, phenoxyethanol, ethylhexyl glycerin, tetrahydroxypropyl ethylenediamine, Aloe Barbadensis, carboxymethyl hydroxyehylcellulose, bisabolol, PEG-45M, and tocopheryl acetate.

In certain embodiments, the carbomer in the composition can be about 2% of the total weight. In certain other embodiments, the ethylhexyl palmitate can be about 5% of the total weight. In certain other embodiments, the cetearyl alcohol and the ceteareth-20 can be about 2.9% of the total weight. In certain other embodiments, the propanediol can be about 2.5% of the total weight. In certain other embodiments, the tetrahydroxypropyl ethylenediamine can be from about 0.5% of the total weight. In certain other embodiments, butylene glycol can be from about 3.5% to about 5% of the total weight. In certain other embodiments, the isododecane can be from about 3% to about 4% of the total weight. In certain other embodiments, the stearic acid can be from about 3% to about 3.5% of the total weight. In certain other embodiments, the ethyl alcohol can be from about 3% to about 4.5% of the total weight. In certain other embodiments, the phenoxyethanol and the ethylhexylglycerin can be from about 0.95% to about 0.97% of the total weight. In certain other embodiments, the carboxymethyl hydroxyehylcellulose can be from about 0.30% to about 0.35% of the total weight. In certain other embodiments, the bisabolol can be about 0.08% of the total weight. In certain other embodiments, the tocopheryl acetate can be from about 0.1% to about 0.2% of the total weight.

Other aspects, embodiments, and features will be apparent from the following description, the drawings, and the claims.

DETAILED DESCRIPTION

Disclosed herein are shaving cream formulations that extend the life of shaving blades.

A shaving cream composition can include water, carbomer, a palmitate ester, a glycerin, glyceryl acrylate/acrylic acid, a C8-C24 hydrocarbon, a fatty acid, butylene glycol, a C1-C4 alcohol, a fatty alcohol, a polyoxyethylene ether, a C3-C6 diol, Brassica Campestris, phenoxyethanol, tetrahydroxypropyl ethylenediamine, Aloe Barbadensis, carboxymethyl hydroxyehylcellulose, a monocyclic sesquiterpene alcohol, tocopheryl acetate, or any combinations thereof.

A palmitate ester can be ethylhexyl palmitate. A C8-C24 hydrocarbon can be isododecane. A fatty acid can be a saturated fatty acid or an unsaturated fatty acid. A saturated fatty acid can be caprylic acid, capric acid, lauric acid, myristic acid, palmitic acid, stearic acid, arachidic acid, behenic acid, lignoceric acid, or cerotic acid. An unsaturated fatty acid can be myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, ordocosahexaenoic acid.

A C1-C4 alcohol can be methyl alcohol, ethyl alcohol, propyl alcohol, or butyl alcohol.

A fatty alcohol can be tert-butyl alcohol, tert-amyl alcohol, 3-methyl-3-pentanol, ethchlorvynol, 1-octanol, 2-ethyl hexanol, pelargonic alcohol, 1-decanol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, nonadecyl alcohol, arachidyl alcohol, heneicosyl alcohol, behenyl alcohol, erycyl alcohol, lignoceryl alcohol, ceryl alcohol, 1-heptacosanol, montanyl alcohol, 1-nonacosanol, myricyl alcohol, 1-dotriacontanol, geddyl alcohol, oleyl alcohol, or cetearyl alcohol.

A polyoxyethylene ether can be a polyoxyethylene ether of a mixture of high molecular mass saturated fatty alcohols, such as ceteareth-n (where n is a number). The number n indicates the average number of ethylene oxide residues in the polyoxyethylene chain. Ceteareth-n can be ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-15, ceteareth-16, ceteareth-17, ceteareth-18, ceteareth-20, ceteareth-22, ceteareth-23, ceteareth-25, ceteareth-27, ceteareth-28, ceteareth-29, ceteareth-30, ceteareth-33, ceteareth-34, ceteareth-40, ceteareth-50, ceteareth-55, ceteareth-60, ceteareth-80, or ceteareth-100.

A C3-C6 diol can be a propanediol, a butanediol, a pentane diol, or a hexanediol.

The formulation can include water, carbomer, ethylhexyl palmitate, glycerin, glyceryl acrylate/acrylic acid, isododecane, stearic acid, butylene glycol, ethyl alcohol, cetearyl alcohol, ceteareth-20, propanediol, *Brassica Campestris*, phenoxyethanol, ethylhexyl glycerin, tetrahydroxypropyl ethylenediamine, *Aloe Barbadensis*, carboxymethyl hydroxyehylcellulose, bisabolol, PEG-45M, and tocopheryl acetate.

A carbomer is an expanded molecule obtained by insertion of a $C_2$ unit in a given molecule. The Carbomers are white, fluffy powders but are frequently used as gels in cosmetics and personal care products. Carbomers can be found in a wide variety of product types including skin, hair, nail, and makeup products, as well as dentifrices. The Carbomers help to distribute or suspend an insoluble solid in a liquid. They are also used to keep emulsions from separating into their oil and liquid components. Carbomers are often used to control the consistency and flow of cosmetics and personal care products. The Carbomers are large molecules prepared from relatively small chemical compounds called monomers. The monomers used to make Carbomer polymers are acrylic acid and polyalkenyl polyethers. The Carbomers are all chemically similar, differing from each other in molecular weight and viscosity. Carbomers have the ability to absorb and retain water, and these polymers can swell to many times their original volume.

Ethylhexyl palmitate, also called octyl pamitate is the fatty acid ester derived from 2-ethylhexanol and palmitic acid, a clear liquid derived from palm oil. Ethylhexyl palmitate is an emollient that gives skin a soft and smooth appearance. Ethylhexyl palmitate is used in cosmetic formulations as a solvent, carrying agent, pigment wetting agent, fragrance fixative and emollient. It has a dry-slip feel that is similar to silicone's texture. For this reason, it is often used as a substitute for silicones in cosmetic products. In addition, Octyl Palmitate is used in beauty products as thickener and solvent. Octyl Palmitate is comedogenic and can cause breakouts. In addition, it can also cause irritations.

Cetostearyl alcohol, cetearyl alcohol or cetylstearyl alcohol is a mixture of fatty alcohols, consisting predominantly of cetyl and stearyl alcohols and is classified as a fatty alcohol. It is used as an emulsion stabilizer, opacifying agent, and foam boosting surfactant, as well as an aqueous and nonaqueous viscosity-increasing agent. It imparts an emollient feel to the skin and can be used in water-in-oil emulsions, oil-in-water emulsions, and anhydrous formulations. It is commonly used in hair conditioners and other hair products.

Tetrahydroxypropyl ethylenediamine (THPE; Chelating Agent) is a substance that is added to cosmetic products to inactivate and to form complexes with metal ions which could affect the stability and/or appearance of cosmetics. THPE has been described to induce keratinocytes' morphological changes in vitro. This clinical study demonstrated that the effect of a 2.5% THPE-containing cream on the keratinocytes cells leads to an immediate and long-term clinical improvement of the skin appearance (radiance and skin firmness, skin lifting). See, Bertin C., Nkengne A., Da Cunha A., Issachar N., and Rossi A., Clinical evidence for the activity of tetrahydroxypropyl ethylenediamine (THPE), a new anti-aging active cosmetic, J Drugs Dermatol. 2011 October; 10(10): 1102-5.

EXAMPLES

Formulation 1

| MANUFACTURER | TRADE NAME | % W/W | MATERIAL COMPOSITION (INCI) | % W/W COMPOSITION |
|---|---|---|---|---|
| INHOUS | WATER (Aqua) | 45.22 | Water (Aqua) | 100.00 |
| NOVEON | CARBOMER 1342 (2% SOLUTION) | 17.50 | Water (Aqua) | 98.00 |
| | | | Carbomer | 2.00 |
| EASTMA | ETHYLHEXYL PALMITATE (Eastman GEM) | 5.00 | Ethylhexyl (Octyl) Palmitate | 100.00 |
| OXEA | BUTYLENE GLYCOL | 5.00 | Butylene Glycol | 100.00 |
| ISP | LUBRAJEL DV FREE | 4.75 | Glycerin | 65.00 |
| | | | Glyceryl Acrylate/Acrylic Acid Copo | 35.00 |
| REMET | SDA 40-B 200 PROOF | 4.50 | SD Alcohol 40B (Ethyl Alcohol) | 100.00 |
| PENREC | VERSAGEL M-1600 | 3.00 | Isododecane | 100.00 |
| NEXEOS | STEARIC ACID | 3.00 | Stearic Acid | 100.00 |
| LIPO | PROMULGEN D (Cetearyl + Ceteareth-20) | 2.90 | Cetearyl Alcohol | 60.00 |
| | | | Ceteareth-20 | 40.00 |
| DUPONT | ZEMEA (Propanediol) | 2.50 | Propanediol "Zemea" | 100.00 |
| VITUSA | GLYCERIN 99.7% USP | 2.50 | Glycerin | 100.00 |
| | GLOSSAMER | 2.00 | *Brassica Campestris* (Rapeseed)/Aleu | 100.00 |
| EMDIND | EUXYL PE-9010 | 0.95 | Phenoxyethanol | 60.00 |
| | | | Ethylhexylglycerin | 40.00 |
| BASF | NEUTROL TE (TETRAHYD/PRO ETHYL/DAMN) | 0.50 | Tetrahydroxypropyl Ethylenediamine | 100.00 |
| AQUALO | SODIUM CMC (morse at ½ level) | 0.30 | Carboxymethyl Hydroxyethylcellulose | 100.00 |
| ORCHID | GET CO ORCHIDIA MENS SHAVE 900656 | 0.15 | Fragrance (Parfum) | 100.00 |
| TERRY | *ALOE VERA* 10X (COSMETIC GRADE) | 0.10 | *Aloe Barbadensis* (*Aloe Vera*) Leaf J | 100.00 |
| BASF | BISABOLOL | 0.08 | Bisabolol | 100.00 |
| DOW | PEG-45 (POLYOX WSR N-60K or PEO-8) | 0.02 | PEG-45M | 100.00 |
| ROCHE | VIT E ACETATE (Tocopheryl Acetate) | 0.01 | Tocopheryl Acetate (Vitamin E Aceta | 100.00 |
| LCW | FD&C BLUE #1 (2% SOLUTION) | 0.01 | Water (Aqua) | 98.00 |
| | | | Blue 1 (Cl#42090) | 2.00 |
| LCW | GAR FD&C GREEN #3 (2% SOL) | 0.01 | Water (Aqua) | 98.00 |
| | | | Green 3 (Cl#42053) | 2.00 |

Formulation 2

| MANUFACTURER | TRADE NAME | % W/W | MATERIAL COMPOSITION (INCI) | % W/W COMPOSITION |
|---|---|---|---|---|
| INHOUS | WATER (Aqua) | 45.61 | Water (Aqua) | 100.00 |
| NOVEON | CARBOMER 1342 (2% SOLUTION) | 17.50 | Water (Aqua) | 98.00 |
| | | | Carbomer | 2.00 |
| EASTMA | ETHYLHEXYL PALMITATE (Eastman GEM) | 5.00 | Ethylhexyl (Octyl) Palmitate | 100.00 |
| ISP | LUBRAJEL DV FREE | 4.25 | Glycerin | 65.00 |
| | | | Glyceryl Acrylate/Acrylic Acid Copo | 35.00 |
| PENREC | VERSAGEL M-1600 | 3.80 | Isododecane | 100.00 |
| NEXEOS | STEARIC ACID | 3.50 | Stearic Acid | 100.00 |
| VITUSA | GLYCERIN 99.7% USP | 3.50 | Glycerin | 100.00 |
| OXEA | BUTYLENE GLYCOL | 3.50 | Butylene Glycol | 100.00 |
| REMET | SDA 40-B 200 PROOF | 3.00 | SD Alcohol 40B (Ethyl Alcohol) | 100.00 |
| LIPO | PROMULGEN D (Cetearyl + Ceteareth-20) | 2.90 | Cetearyl Alcohol | 60.00 |
| | | | Ceteareth-20 | 40.00 |
| DUPONT | ZEMEA (Propanediol) | 2.50 | Propanediol "Zemea" | 100.00 |
| | GLOSSAMER | 2.30 | *Brassica Campestris* (Rapeseed)/Aleu | 100.00 |
| EMDIND | EUXYL PE-9010 | 0.97 | Phenoxyethanol | 60.00 |
| | | | Ethylhexylglycerin | 40.00 |
| BASF | NEUTROL TE (TETRAHYD/PRO ETHYL/DAMN) | 0.50 | Tetrahydroxypropyl Ethylenediamine | 100.00 |
| TERRY | *ALOE VERA* 10X (COSMETIC GRADE) | 0.50 | *Aloe Barbadensis* (*Aloe Vera*) Leaf J | 100.00 |
| AQUALO | SODIUM CMC (morse at ½ level) | 0.35 | Carboxymethyl Hydroxyethylcellulose | 100.00 |
| ORCHID | GET CO ORCHIDIA MENS SHAVE 900656 | 0.15 | Fragrance (Parfum) | 100.00 |
| BASF | BISABOLOL | 0.08 | Bisabolol | 100.00 |
| DOW | PEG-45 (POLYOX WSR N-60K or PEO-8) | 0.04 | PEG-45M | 100.00 |
| ROCHE | VIT E ACETATE (Tocopheryl Acetate) | 0.02 | Tocopheryl Acetate (Vitamin E Aceta | 100.00 |
| LCW | FD&C YELLOW #5 (2% SOLUTION) | 0.01 | Water (Aqua) | 98.00 |
| | | | Yellow 5 (Cl#19140) | 2.00 |
| LCW | FD&C BLUE #1 (2% SOLUTION) | 0.01 | Water (Aqua) | 98.00 |
| | | | Blue 1 (Cl#42090) | 2.00 |
| LCW | GAR FD&C GREEN #3 (2% SOL) | 0.01 | Water (Aqua) | 98.00 |
| | | | Green 3 (Cl#42053) | 2.00 |
| FRAGRANCE | | | | |

Procedures for Making Formulations

Formulation 2 was prepared by following procedures: first phase included water (45.6 wt %) and Lubragel CV free (4.25 wt %) and the batch was mixed for 15-20 min with vortex.

Second phase was premixed cold for 15-20 min until smooth and uniform. The second phase ingredients include glycerine (3.5 wt %), butylene glycol (3.5 wt %), Zemea (propanediol) (2.5 wt %), sodium CMC (0.35 wt %), and PEG-45 (Polyox WSR N-60K or PEO-8) (0.04 wt %). The premixed second phase was added to the batch and the batch was heated to 75° C. while mixing. The batch was mixed with moderate vortex speed.

Third phase was heated to 75° C. and added to the batch. The third phase ingredients included promulgen D (cetearyl+ceteareth-20) (2.9 wt %), stearic acid (3.5 wt %), glossamer L-6600 (2.3 wt %), versagel M-1600 (3.8 wt %), ethylhexyl(octyl) palmitate (5.0 wt %), and vitamine E acetate (tocopheryl acetate) (0.02 wt %). The batch was mixed with vortex for 15-20 min.

Fourth phase included carbomer 1342 (2% solution) (17.50 wt %) and was added to the batch and mixed for 15-20 min. If necessary, batch was made sure to warm to 70° C.

Fifth phase included neutrol TE (tetrahyd/PRO ethyl/DAMN) (0.50 wt %) and was added to the batch, mixed for 15-20 min, and cooled to batch to 40° C.).

Sixth phase included Euxyl PE-9010 (phenoxy ethnaol/ethylhexyglycerin) and was added to the batch and mixed until smooth.

Seventh phase included GAR FD&C green #3 (2% solution) (0.01 wt %), FD&C blue #1 (2% solution) (0.01 wt %), and FD&C yellow #5 (2% solution) (0.01 wt %) and was added to the batch. Final color was light blue/green. Appearance was opaque, viscous-lotion type, free of foreign matter. Final pH was 5.00-6.00 at 25° C., viscosity was 36,000-44,000 cP at 25° C., and specific gravity was 0.94-1.00 at 25° C. Microbiology results showed NMT 100 CFU/gm with gram negative absent.

Product Testing

A randomized, single-blind, cross-over, single-center test trial has been conducted for 16 weeks in accordance with the Declaration of Helsinki, the ICH guideline E6 for *Good Clinical Practice*, the requirement of 21 CFR Parts 50 and 56, other applicable laws and regulations, the Consumer Product Testing Company (CPTC) Standard Operating Procedures, and the approval protocol.

To evaluate if the life of a razor blade is extended with use of Formulation 2 shave cream compare to the comparable product, 35 male subjects, ages 21 to 65 years, were recruited and qualified for this trial. Subject #'s 12, 15, 25 and 32 discontinued their participation due to personal reasons unrelated to test material use. Thirty-one subjects completed the trial.

The subject inclusion criteria were 1) approximately 30 healthy male subjects, ages 21 to 5 years, inclusive; 2) subjects who shaved daily with a blade razor; 3) subjects who read, understood, and signed an Informed Consent Form that included a HIPAA statement, and 4) subjects who were considered dependable and able to follow directions, as outlines in the protocol.

The subject exclusion criteria were 1) subjects in ill health or taking medication which could have influenced the purpose, integrity or outcome of the trial; 2) subjects who used any new cosmetic, toiletry or personal care product during the course of the trial; 3) subjects currently using any systemic or topical corticosteroids, anti-inflammatory drugs, antihistamines, retinoids or other medication that, in the opinion of Investigator, may have influence the outcome of the trial; 4) subjects who had a history of acute or chronic dermatologic conditions; and 5) subjects having any visible skin disease, which might have been confused with a skin reaction from the test material.

Test materials included 1) shaving cream with Formulation 2; 2) a commercial shave gel; and 3) commercial manual razor.

Start Phase I (Baseline)

All subjects were examined by an Expert Grader for observations of any type of visible facial skin disease which could prohibit them from participation in this trial. Acceptable subjects were divided into two groups. Approximately one-half of the subjects (Group #1) received a manual razor and shaving cream with Formulation 2. The remaining one-half of subjects (Group #2) received the same manual razor as Group #1 and a commercial shave gel. Group assignment was based upon a randomization supplied by Consumer Product Testing Company, Inc.

Subjects were supplied with the test material and were instructed to use the test material daily for the next 8 weeks when shaving, according to the following instructions:

1. Discontinue the use of your current blade razor and shaving materials and us only the supplied blade razor and shaving cream/gel for the duration of this trial. Do not introduce any new cleansing products or other toiletries during the trial.
2. Shave daily using the supplied blade razor and shaving cream/gel.
3. Keep out of reach of children.
4. Do not let anyone else use the test material.
5. Record the times of use on the daily diary.
6. Report any adverse reactions or problems immediately to the Testing Facility Staff
7. You will be issued a daily diary to document when you shave your face. After each daily shave, you will rate the comfort level of the shave according to a scale on the daily diary, 1=very comfortable and 5=very uncomfortable. If you rate your shave as "5" (uncomfortable), you will discontinue using the supplied razor and shaving cream/gel and you will begin to use your own razor and shaving materials until your scheduled week 8 visit to the Testing Facility. You will be given a questionnaire to complete at home.
8. Answer question #1 after week 1 is completed and answer questions 2-7 after week 2 is completed.
9. If you have rated your shave as "5" very uncomfortable, do not record any entries on the daily diary while using your current razor blade and shaving materials.
10. After 8 weeks, you will return to the Testing Facility with the razor, used blade, shaving cream/gel, diary, and completed questionnaire.

End Phase I/Start Phase II (Week 8)

Subjects returned to the Testing Facility at the conclusion of the 8 week use period and returned any unused test material and the razor. Daily diaries were reviewed for completeness prior to distribution of Phase II tests materials. Test material distribution was randomized, as previously described. Subjects were provided with the test material that they had not used. The instructions for use remained unchanged.

Each subject received a new daily diary to document shaving and to rate their shave comfort. Subjects also received Sponsor-supplied questionnaire to be completed after week 1 and 2 of Phase II, as previously described.

End Phase II (Week 16)

Subjects returned to the Testing Facility at the conclusion of the 16 week trial interval (after the second 8 week use period). Razors, test materials and completed diaries and questionnaires were returned and reviewed for completeness prior to the subjects' dismissal.

Test Results

Statistically significant differences in the percentage of total subjects was observed between the two test materials in regards to the average life of the blade (approximately 32 days) and comfort rating after 56 days of use (approximately 2.45). Test material, Formulation 2 had a statistically significantly lower percentage of subjects reach comfort level 5 than test material, the commercial shave gel, and a statistically significantly higher percentage of subjects reaching day 56 while maintaining a comfortable shave. See FIGS. 1-5 and Table 1.

TABLE 1

Test results (comfort scale: 1 = very comfortable to 5 = very uncomfortable)

| | Day Comfort Rating Reached 5 | | Comfort Rating After Phase Completion | | |
|---|---|---|---|---|---|
| Test Material | Commercial shaving gel | Formulation 2 | Test Material | Commercial shaving gel | Formulation 2 |
| Average Days | 33.7 | 31.7 | Average Comfort | 2.5 | 2.4 |
| Min | 18 | 23 | Min | 1 | 1 |
| Max | 49 | 48 | Max | 4 | 4 |
| # of Subjects | 21 | 3 | # of Subjects | 2 | 32 |
| % of Total | 67.7% | 8.6% | % of Total | 6.5% | 91.4% |
| P Value | <0.001 | | P Value | <0.001 | |
| Significance | Yes | | Significance | Yes | |

Figure 1:
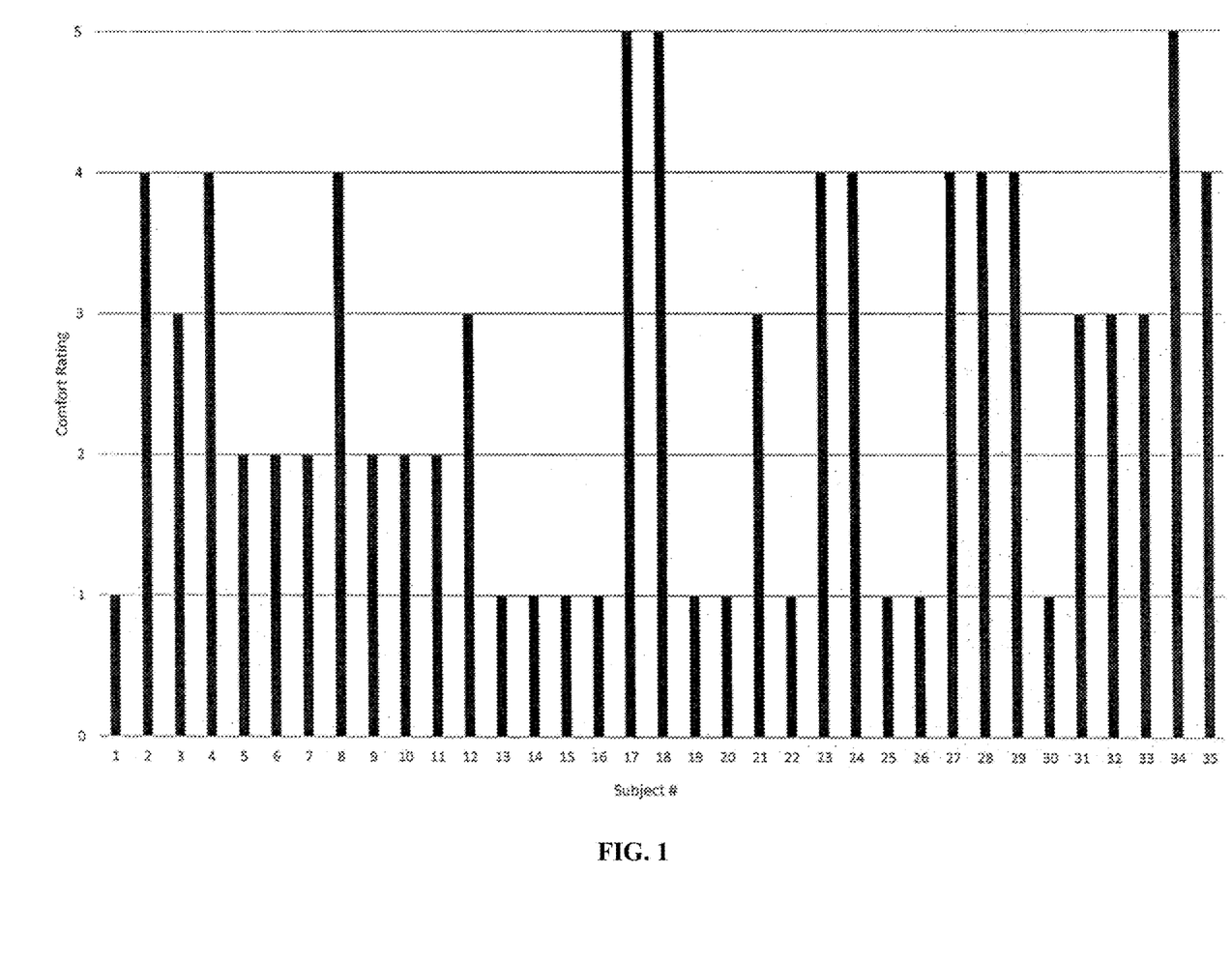
FIG. 1 is a graph depicting the individual comfort rating of the Formulation 2 from all subjects.
Figure 2:
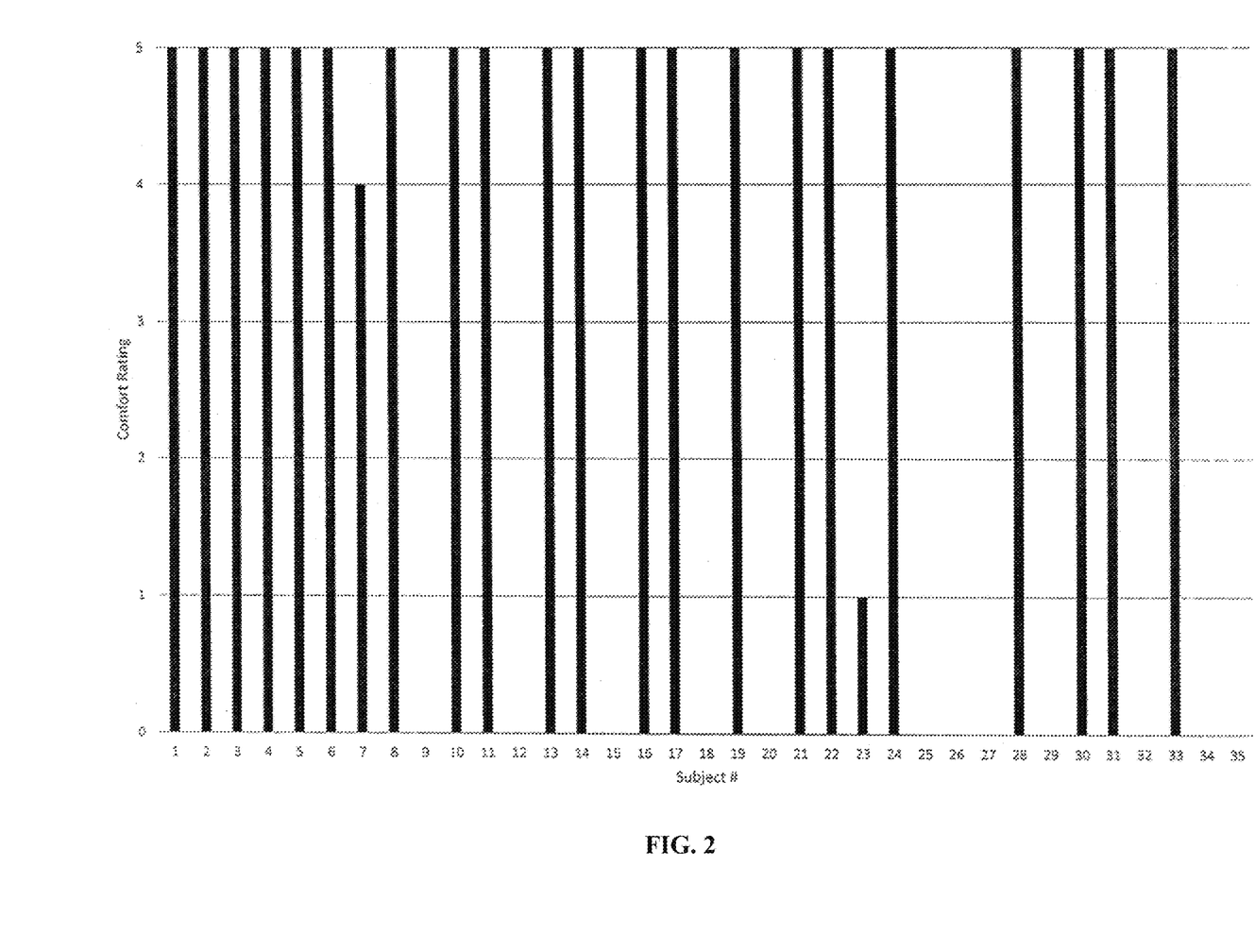
FIG. 2 is a graph depicting the individual comfort rating of a commercial shaving gel from all subjects.

FIGS. 1 and 2 exhibit bar graphs of the comfort ratings. Formulation 2 exhibited more subjects rating a higher level of comfort on day 56 than the commercial shaving gel. The bar graph shows each individual's response to the comfort rating on day 56.

Figure 3:
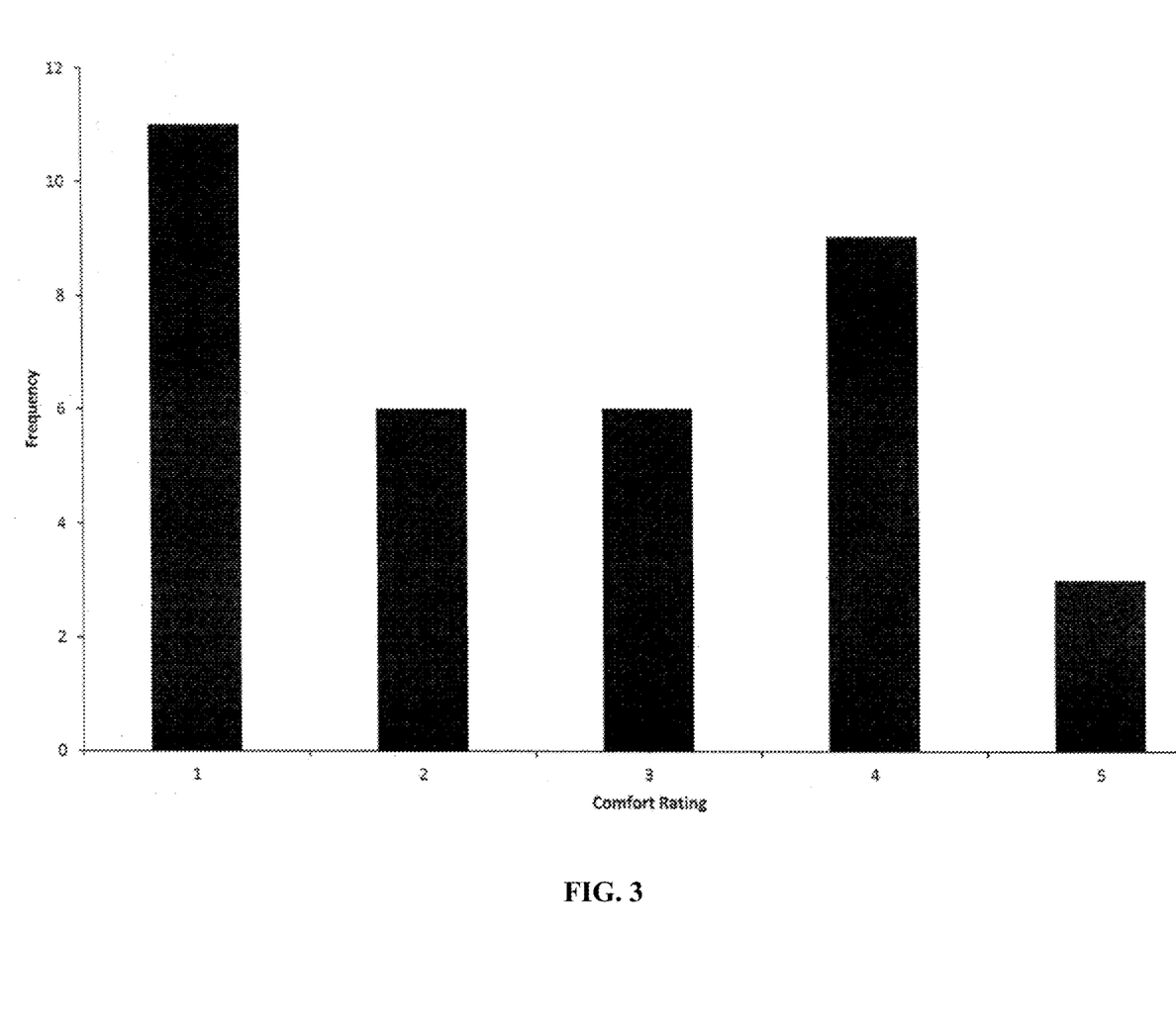
FIG. 3 is a graph depicting the summary of comfort rating of the Formulation 2.
Figure 4:
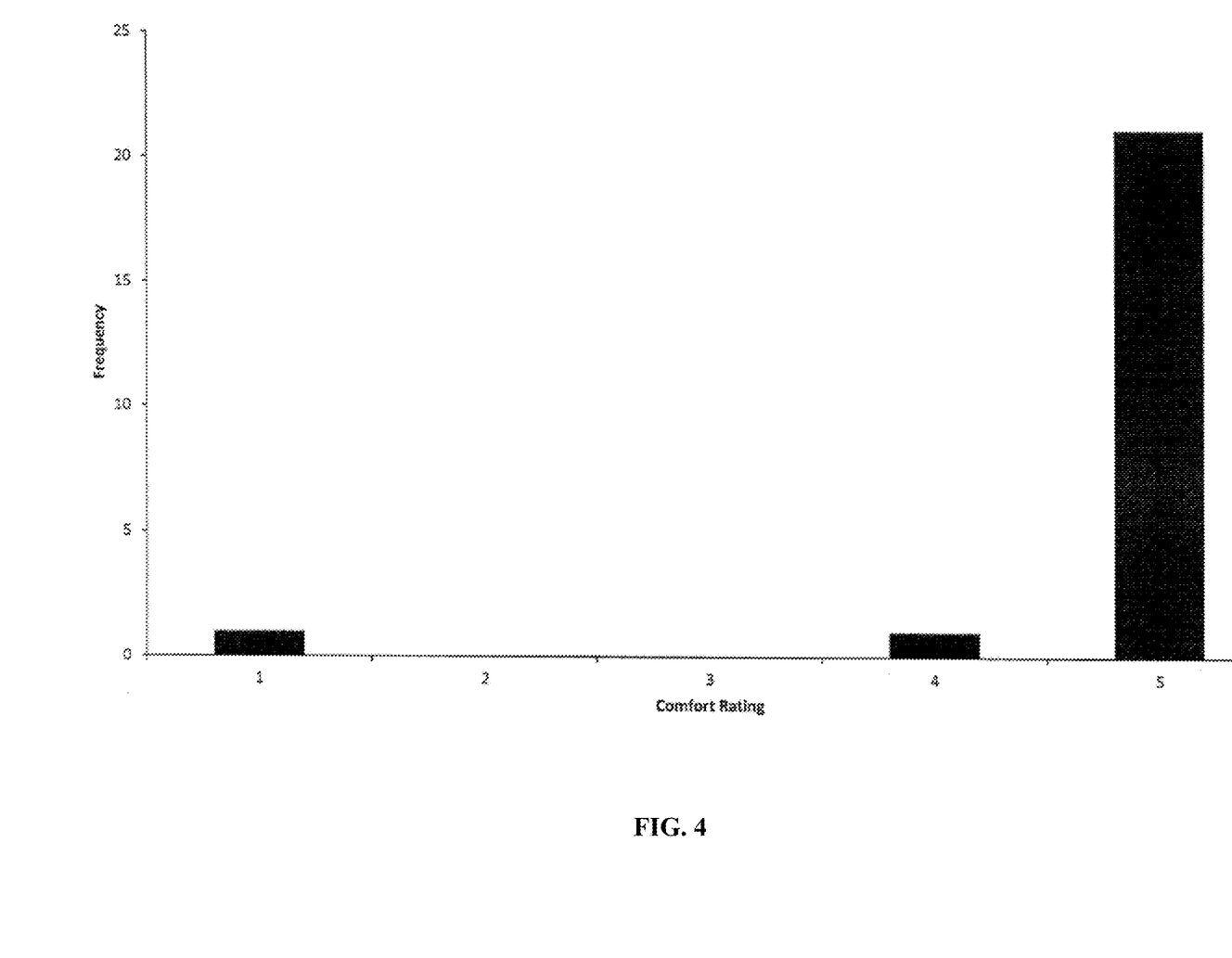
FIG. 4 is a graph depicting the summary of comfort rating of a commercial shaving gel.

FIGS. 3 and 4 are histograms of these same comfort ratings. As observed in the histograms, Formulation 2 exhibited only three subjects reach a comfort rating of "5" (very uncomfortable) out of 35 subjects, while the commercial shaving gel exhibited 21 subjects reach a comfort rating of "5" by day 56. Of the 35 subjects, 11 subjects exhibited a comfort rating "1" at day 56 while using Formulation 2, and only one subject exhibited a comfort rating "1" at day 56 while using the commercial shaving gel.

Figure 5:
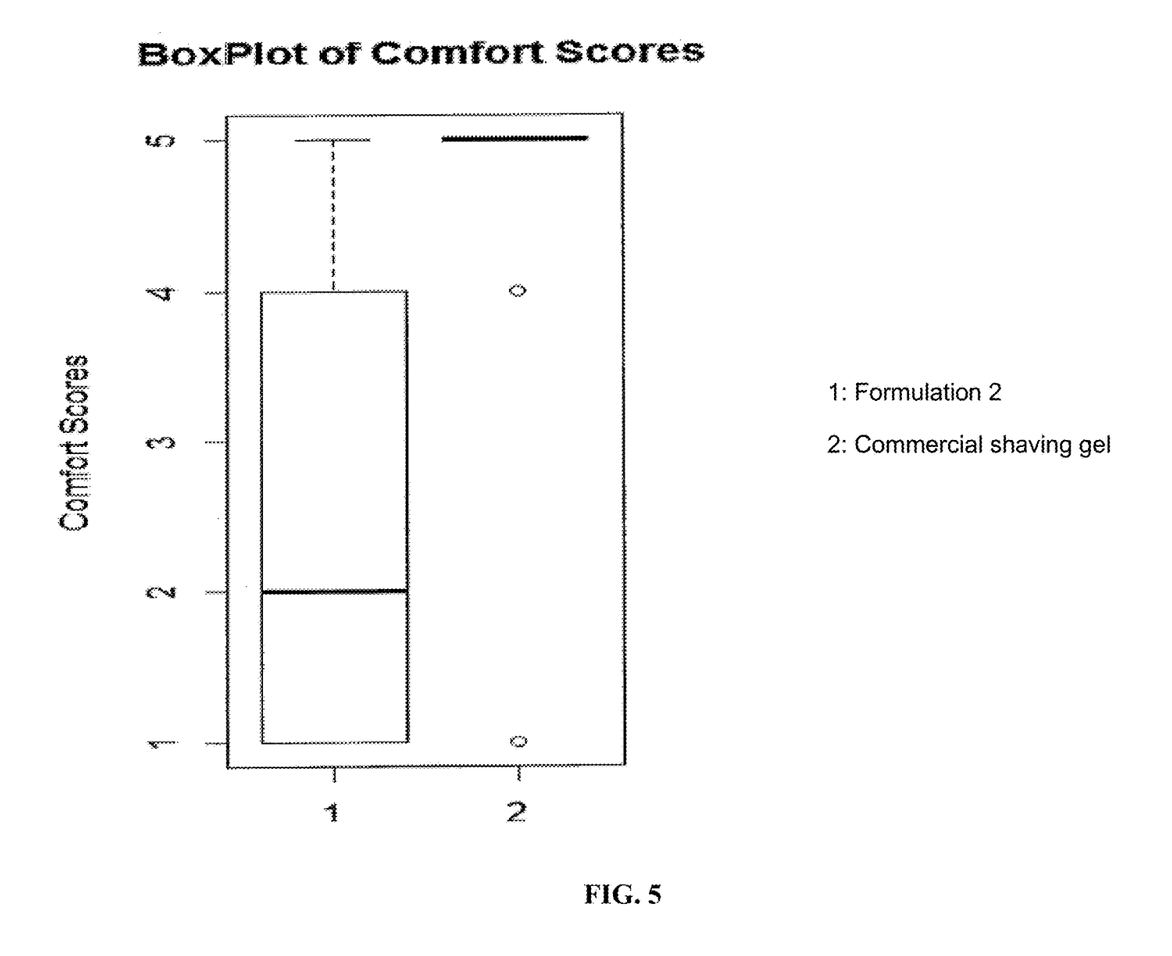
FIG. 5 is a boxplot of comfort scores for the Formulation 2 and a commercial shaving gel.

FIG. 5 displays boxplots of both test materials' comfort rating data. Formulation 2 had a median comfort rating of "2," with the first quartile at "1" and the third quartile at "4." The commercial shaving gel exhibited a median, first quartile, and third quartile comfort rating of "5," with outliers present at comfort ratings of "1" and "4."

In conclusion, based on all the statistical analysis performed between the two test materials, Formulation 2 exhibited a significantly more comfortable and longer lasting effect than the commercial shaving gel.

Other embodiments are within the scope of the following claims.

What is claimed is:

1. A shaving cream composition comprising:
water, carbomer, ethylhexyl palmitate, glycerin, glyceryl acrylate/acrylic acid, isododecane, stearic acid, butylene glycol, ethyl alcohol, cetearyl alcohol, ceteareth-20, propanediol, *Brassica Campestris*, phenoxyethanol, ethylhexyl glycerin, tetrahydroxypropyl ethylenediamine, *Aloe Barbadensis*, carboxymethyl hydroxyehylcellulose, bisabolol, PEG-45M, and tocopheryl acetate, wherein the carbomer is about 2% of the total weight, the ethylhexyl palmitate is about 5% of the total weight, the cetearyl alcohol and the ceteareth-20 are about 2.9% of the total weight, wherein the propanediol is about 2.5% of the total weight, the tetrahydroxypropyl ethylenediamine is from about 0.5% of the total weight, the butylene glycol is from about 3.5% to about 5% of the total weight, the isododecane is from about 3% to about 4% of the total weight, the stearic acid is from about 3% to about 3.5% of the total weight, the ethyl alcohol is from about 3% to about 4.5% of the total weight, the phenoxyethanol and the ethylhexylglycerin are from about 0.95% to about 0.97% of the total weight, the carboxymethyl hydroxyethylcellulose is from about 0.30% to about 0.35% of the total weight, the bisabolol is about 0.08% of the total weight, and the tocopheryl acetate is from about 0.1% to about 0.2% of the total weight.

2. A shaving cream composition comprising:
water, carbomer, a palmitate ester, a glycerin, glyceryl acrylate/acrylic acid, a C8-C24 hydrocarbon, a fatty acid, butylene glycol, a c1-c4 alcohol, a fatty alcohol, a polyoxyethylene ether, a C3-C6 diol, *Brassica Campestris*, phenoxyethanol, tetrahydroxypropyl ethylenediamine, *Aloe Barbadensis*, carboxymethyl hydroxyethylcellulose, a monocyclic sesquiterpene alcohol, and tocopheryl acetate, wherein the carbomer is about 2% of the total weight, the palmitate ester is about 5% of the total weight, the cetearyl alcohol and the ceteareth-20 are about 2.9% of the total weight, wherein the propanediol is about 2.5% of the total weight, the tetrahydroxypropyl ethylenediamine is from about 0.5% of the total weight, and the tocopheryl acetate is from about 0.1% to about 0.2% of the total weight.

3. A method of extending blade life comprising:
contacting a blade with a composition of any one of claim 1 or 2.

* * * * *